United States Patent
Milana-Panopoulos

[11] Patent Number: 5,944,682
[45] Date of Patent: Aug. 31, 1999

[54] COMBINATION PATELLAR BANDAGE AND KNEE BRACE

[76] Inventor: Maria Milana-Panopoulos, 1327 Kinsmere Dr., New Port Richey, Fla. 34655

[21] Appl. No.: 09/088,014

[22] Filed: Jun. 1, 1998

[51] Int. Cl.[6] .................................................... A61F 13/00
[52] U.S. Cl. ................................. 602/62; 602/26; 602/57
[58] Field of Search .............................. D24/189; 602/26, 602/60, 61, 62, 63, 41–59, 21; 604/180

[56] References Cited

U.S. PATENT DOCUMENTS

| | | | |
|---|---|---|---|
| 3,439,676 | 4/1969 | Burda | 602/79 X |
| 3,490,448 | 1/1970 | Grubb | 602/46 |
| 4,176,664 | 12/1979 | Kalish | 602/58 X |
| 4,201,203 | 5/1980 | Applegate | 602/26 |
| 4,287,884 | 9/1981 | Applegate | 602/26 |
| 4,287,885 | 9/1981 | Applegate | 602/26 |
| 5,503,908 | 4/1996 | Faass | 428/198 |
| 5,556,374 | 9/1996 | Grace et al. | 602/26 |
| 5,613,943 | 3/1997 | Palumbo | 602/62 |
| 5,711,312 | 1/1998 | Staudinger | 128/845 |
| 5,728,057 | 3/1998 | Ouellette et al. | 602/62 |
| 5,759,167 | 6/1998 | Shields, Jr. et al. | 602/26 |
| 5,820,578 | 10/1998 | Johansen | 602/57 |

*Primary Examiner*—Richard J. Apley
*Assistant Examiner*—Kim M. Lee
*Attorney, Agent, or Firm*—Stanley M. Miller

[57] ABSTRACT

A bandage adapted to be wrapped around a knee has a first side covered with a pressure-sensitive adhesive. A "U"-shaped housing is secured to the adhesive and is aligned so that a longitudinal axis of symmetry of the housing is coincident with a longitudinal axis of symmetry of the bandage. A flexible and resilient "U"-shaped patellar support member of foam construction is housed within the housing and supports a patella from three sides when the bandage is properly applied with its longitudinal axis encircling the knee. A slit is formed in the housing so that the patellar support member can be removed from the housing for subsequent re-use with another bandage. The adhesive is covered by a peelable cover that is removed and discarded just prior to bandage use.

3 Claims, 2 Drawing Sheets

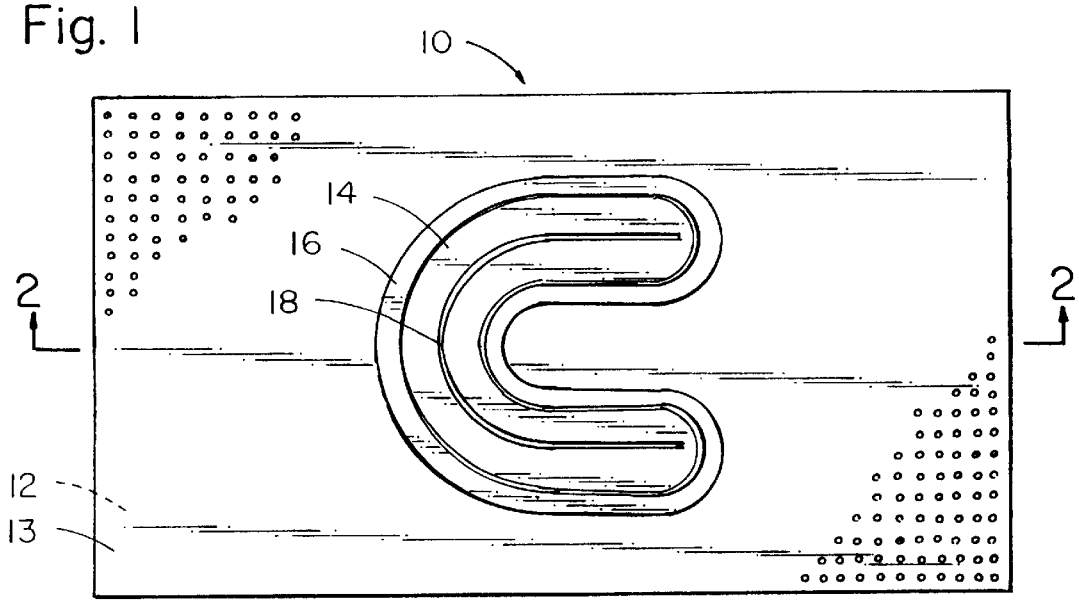
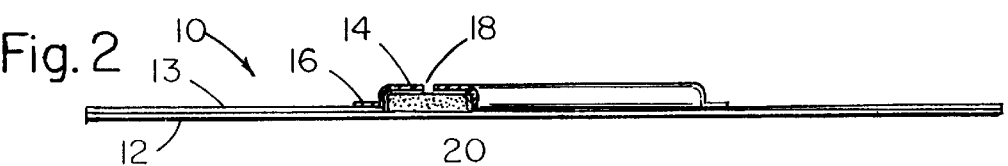
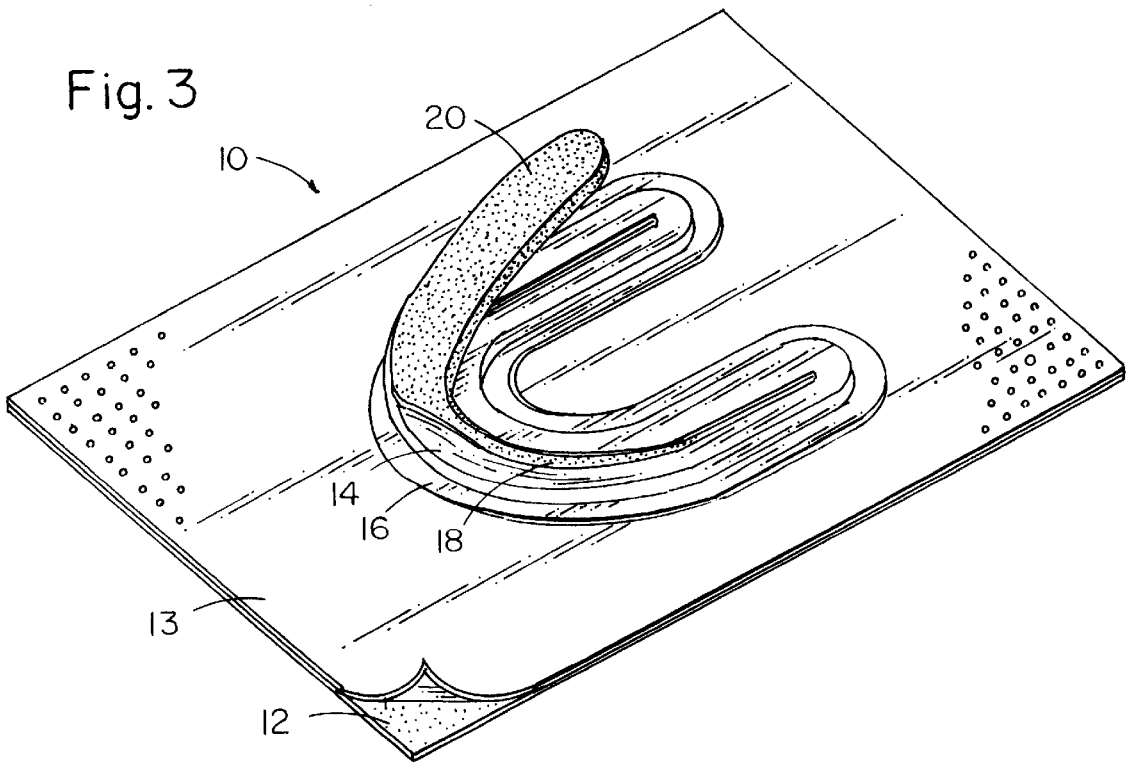

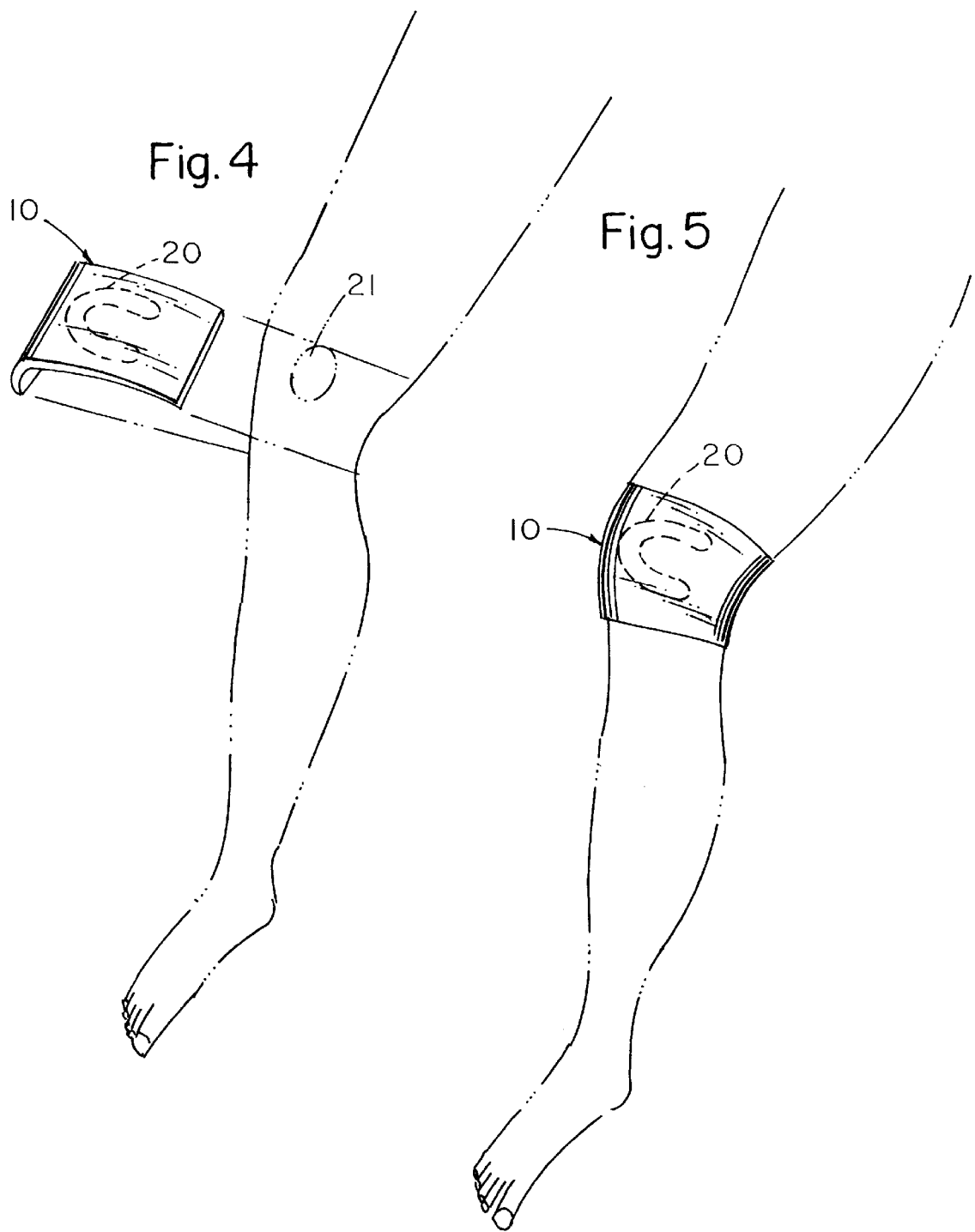

COMBINATION PATELLAR BANDAGE AND KNEE BRACE

BACKGROUND OF THE INVENTION

1. Field of the Invention

This invention relates generally, to medical appliances. More particularly, it relates to a knee bandage that provides support for a knee cap.

2. Description of the Prior Art

A conventional bandage has a self-adhesive surface covered by a protective film that is peeled off when the bandage is to be applied to the skin of a patient or trauma victim. Typically, a square or rectangular piece of gauze is adhered to the bandage, mid-length thereof; the gauze may be covered by the protective film, covered by an extension of the protective film, or left uncovered.

A piece of gauze is quite thick relative to the thickness of a bandage. Accordingly, a conventional bandage is not ideally suited for knee injuries because the gauze can displace the patella, causing or aggravating an injury thereto.

What is needed, then, is a bandage having special utility as a knee bandage. The needed bandage would not cause displacement of the patella but would support it against movement instead.

However, in view of the art considered as a whole at the time the present invention was made, it was not obvious to those of ordinary skill in this art how the needed improvement could be provided.

SUMMARY OF THE INVENTION

The long-standing but heretofore unfulfilled need for an apparatus that overcomes the limitations of the prior art is now met by a new, useful, and nonobvious invention.

The present invention includes a knee bandage that includes a flexible substrate having a pressure-sensitive adhesive applied to a first side thereof. A "U"-shaped housing is secured to the flexible substrate; the housing has a longitudinal axis parallel to a longitudinal axis of the substrate. A "U"-shaped patellar support means is positioned within the housing and supports a patella on three sides when the flexible substrate is wrapped around a knee with the longitudinal axis of the substrate encircling the knee. The patellar support means preferably takes the form of a flexible and resilient, "U"-shaped foam pad having structural characteristics adequate to support a patella, but it may be formed of other suitable materials.

A protective cover is disposed in overlying relation to the adhesive; it is peelable therefrom when the bandage is to be used. A "U"-shaped cut-out is formed in the protective cover in registration with the housing so that the protective cover does not overlie the housing.

An elongate, "U"-shaped slit means is formed in the housing so that the patellar support means may be introduced into the housing prior to use of the bandage and so that the patellar support means may be removed from the housing after use of the bandage.

Preferably, the longitudinal axis of the bandage is a longitudinal axis of symmetry of the bandage and the longitudinal axis of the patellar support means is coincident with said longitudinal axis of symmetry.

The housing includes a "U"-shaped top wall within which the slit means is formed. The top wall is flat and disposed substantially parallel to the substrate. A vertical side wall depends from peripheral edges of the top wall, and a flange extends from a lowermost end of the vertical side wall in overlying relation to the substrate. The side wall has a preselected height that is substantially equal to a preselected thickness of the patellar support means.

It is a primary object of this invention to provide a knee bandage that supports a patella.

Another object is to provide a patella-supporting knee bandage of elegant construction that is easy and economical to manufacture.

These and other important objects, features, and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 1 is a bottom plan view of an exemplary embodiment of the invention;

FIG. 2 is a sectional view taken along line 2—2 in FIG. 1;

FIG. 3 is a perspective view of the exemplary embodiment;

FIG. 4 is an exploded perspective view of the exemplary embodiment and a knee to which it is to be applied; and FIG. 5 is a perspective view of the exemplary embodiment when in its functional position on a knee.

DETAILED DESCRIPTION OF THE PREFERRED EMBODIMENT

Referring now to FIG. 1, it will there be seen that an exemplary embodiment of the invention is denoted as a whole by the reference numeral 10.

Novel bandage and knee brace 10 includes a perforated, flexible substrate 12 having a first side thereof covered by a pressure-sensitive adhesive. The adhesive is covered by a thin, flexible protective film or cover 13. When cover 13 is peeled off in the manner indicated at the bottom of FIG. 3, the adhesive on bandage 12 is uncovered so that it can adhere to the skin of a patient. Bandage 12 is preferably of elastomeric construction.

As perhaps best understood in connection with FIGS. 2 and 3, a raised enclosure or housing 14 having a generally "U"-shaped configuration is positioned substantially centrally of substrate 12. In a preferred embodiment, a longitudinal axis and preferably the longitudinal axis of symmetry of said "U"-shaped housing is coincident with a longitudinal axis and preferably the longitudinal axis of symmetry of substrate 12.

A flange 16 that circumscribes housing 14 is formed integrally with a vertically disposed side wall of said housing, extends outwardly from a lowermost end thereof, overlies substrate 12, and is adhered to said substrate by the adhesive carried thereby. A "U"-shaped cut-out is formed in cover 13 in registration with said flange so that said flange and hence said raised housing 14 are adhered to said substrate. Accordingly, peeling cover 13 away from substrate 12 does not affect housing 14 or flange 16.

An elongate, "U"-shaped slit 18 is formed in a flat top wall of housing 14, said slit extending substantially the entire length of said housing 14. The slit enables introduction into housing 14 of a "U"-shaped patellar support 20 when the novel bandage 10 is to be used, and said slit allows removal of said patellar support 20 when the bandage is removed from the patient's knee and discarded. In this way, patellar support 20 may be reused. Since it is protectively sealed within housing 14 when in use, it remains clean and suitable for re-use.

Support member 20 is preferably made of a flexible and resilient foam material and has a predetermined thickness; it has a preselected strength sufficient to support a patella.

FIG. 3 depicts novel bandage and knee support 10 when patellar support 20 is being inserted through slit 18 into housing 14. Novel bandage 10 is not used until said patellar support 20 is fully housed within raised enclosure 14.

FIG. 4 depicts appliance 10 when ready for use. Patellar support 20 is housed within enclosure 14 and cover 13 has been peeled from substrate 12. A patella is denoted 21.

FIG. 5 depicts novel appliance 20 in its functional position. Note that patella 21 is positioned intermediate the transversely disposed arms of "U"-shaped patellar support 20. In this way, the patella is supported at its top and bottom and on one side (the medial side) (could be used with the lateral side as well) to enhance the comfort of the patient. Significantly, no part of housing 14 overlies patella 21, thereby ensuring that it will not displace the patella or cause further injury thereto.

It will thus be seen that the objects set forth above, and those made apparent from the foregoing description, are efficiently attained and since certain changes may be made in the foregoing construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A knee bandage, comprising:
    a flexible substrate having a pressure-sensitive adhesive applied to a first side thereof;
    said flexible substrate having a longitudinal axis;
    a "U"-shaped housing secured to said flexible substrate;
    said "U"-shaped housing having a longitudinal axis parallel to the longitudinal axis of said substrate;
    a "U"-shaped patellar support means positioned within said housing; and
    an elongate, "U"-shaped slit means formed in said housing so that said patellar support means may be introduced into said housing prior to use of said bandage and so that said patellar support means may be removed from said housing after use of said bandage;
    wherein said flexible substrate is adapted to be wrapped around a knee with said longitudinal axis of said substrate encircling the knee and with said patellar support means supporting the patella on three sides.

2. The bandage of claim 1, wherein said housing includes a "U"-shaped top wall within which said slit means is formed, said top wall being flat and disposed substantially parallel to said substrate, a vertical side wall that depends from peripheral edges of said top wall, and a flange that extends from a lowermost end of said vertical side wall in overlying relation to said substrate.

3. The bandage of claim 2, wherein said side wall has a preselected height that is substantially equal to a preselected thickness of said patellar support means.

* * * * *